US012146178B2

(12) United States Patent
Guzman, Jr.

(10) Patent No.: US 12,146,178 B2
(45) Date of Patent: Nov. 19, 2024

(54) MICROBIAL CONVERSION OF LACTOSE-CONTAINING FEEDSTOCKS TO CARBOXYLIC ACIDS

(71) Applicant: Capro-X, Inc., Ithaca, NY (US)

(72) Inventor: Juan J. Guzman, Jr., Ithaca, NY (US)

(73) Assignee: Capro-X, Inc., Ithaca, NY (US)

( * ) Notice: Subject to any disclaimer, the term of this patent is extended or adjusted under 35 U.S.C. 154(b) by 574 days.

(21) Appl. No.: 16/801,388

(22) Filed: Feb. 26, 2020

(65) Prior Publication Data

US 2020/0270648 A1 Aug. 27, 2020

Related U.S. Application Data

(63) Continuation of application No. PCT/US2020/019534, filed on Feb. 24, 2020.

(60) Provisional application No. 62/809,685, filed on Feb. 24, 2019.

(51) Int. Cl.
*C12P 7/52* (2006.01)
*C12P 7/56* (2006.01)
*C12P 7/6409* (2022.01)

(52) U.S. Cl.
CPC .................. *C12P 7/52* (2013.01); *C12P 7/56* (2013.01); *C12P 7/6409* (2013.01)

(58) Field of Classification Search
None
See application file for complete search history.

(56) References Cited

U.S. PATENT DOCUMENTS

| 9,650,652 | B2 | 5/2017 | Angenent et al. | |
|---|---|---|---|---|
| 2008/0254165 | A1* | 10/2008 | Patel | C12P 7/56 426/40 |

OTHER PUBLICATIONS

Panesar, Parmjit S., et al. "Bioutilisation of whey for lactic acid production." Food chemistry 105.1 (2007): 1-14. (Year: 2007).*
Durham, Rosalie J. "Modern approaches to lactose production." Dairy-derived ingredients (2009): 103-144, excerpt of Table 5.1 (Year: 2009).*
Kucek, Leo A., Mytien Nguyen, and Largus T. Angenent. "Conversion of L-lactate into n-caproate by a continuously fed reactor microbiome." Water research 93 (2016): 163-171. (Year: 2016).*
Dohan, L. A., et al. "Lactose hydrolysis by immobilized lactase: semi-industrial experience." Enzyme Engineering: vol. 5 (1980): 279-293. (Year: 1980).*
Domingos, Joana M B, et al. "Effect of operational parameters in the continuous anaerobic fermentation of cheese whey on titers, yields, productivities, and microbial community structures." ACS Sustainable Chemistry & Engineering 5.2 (2017): 1400-1407. (Year : 2017).*

Matthew T. Agler et al.; "Chain elongation with reactor microbiomes: upgrading dilute ethanol to medium-chain carboxylates;" May 1, 2012; Energy & Environmental Science (© The Royal Society of Chemistry 2012); pp. 8189-8192.
Catherine M. Spirito et al.; "Chain elongation in anaerobic reactor microbiomes to recover resources from waste;" 2014; www.sciencedirect.com—Current Opinion in Biotechnology; pp. 115-122.
Jiajie Xu et al.; "In-line and selective phase separation of medium-chain carboxylic acids using membrane electrolysis;" Feb. 15, 2015; Royal Society of Chemistry 2015; pp. 6847-6850.
Leo A. Kucek et al.; "Conversion of L-lactate into n-caproate by a continuously fed reactor microbiome;" Dec. 12, 2015; www.elsevier.com/locate/watres—Water Research, pp. 163-171.
Jiajie Xu et al.; "Temperature-Phased Conversion of Acid Whey Waste Into Medium-Chain Carboxylic Acids via Lactic Acid: No External e-Donor;" Feb. 21, 2018; Joule 2; 280-295; Elsevier Inc.; pp. 1-16.
Najafpour et al., "Biological Treatment of Dairy Wastewater in an Upflow Anaerobic Sludge-Fixed Film Bioreactor," American-Eurasian J. Agric. & Environ. Sci., vol. 4, No. 2, 2008. pp. 251-257.
Xu et al., "Temperature-Phased Conversion of Acid Whey Waste Into Medium-Chain Carboxylic Acids via Lactic Acid: No External e-Donor," Joule, vol. 2, No. 2, Feb. 21, 2018 [Retrieved on Apr. 7, 2020]. Retrieved from the Internet: <https://www.sciencedirect.com/science/article/pii/S2542435117301794>. pp. 280-295.
Int'l Application No. PCT/US2020/019534, "Notification of Transmittal of the International Search Report and the Written Opinion of the International Searching Authority, or the Declaration," May 7, 2020, 12 Pgs.
Ana R. Prazeres, et al.; "Cheese whey management: A review"; Journal Of Environmental Management; Jun. 19, 2012; pp. 48-68.
Leo A. Kucek, et al.; "High n-caprylate productivities and specificities from dilute ethanol and acetate: chain elongation with microbiomes to upgrade products from syngas fermentation"; Energy Environ. Sci., 2016, 9, 3482; Sep. 19, 2016; pp. 3482-3494.
Lei Li, et al.; "Anaerobic digestion of food waste: A review focusing on process stability"; Bioresource Technology; 248 (2018) pp. 20-28; Jul. 6, 2017.
Vicky De Groof, et al.; "Medium Chain Carboxylic Acids from Complex Organic Feedstocks by Mixed Culture Fermentation"; Molecules, 2019, 24, 398; doi:10.3390/molecules24030398; pp. 1-32; Jan. 22, 2019 (www.mdpi.com/journal/molecules).
Ashira Roopnarain, et al.; "Unravelling the anaerobic digestion 'black box': Biotechnological approaches for process optimization"; Renewable And Sustainable Energy Reviews; 152 (2021) 111717; pp. 1-21; Oct. 1, 2021.

(Continued)

*Primary Examiner* — Robert J Yamasaki
(74) *Attorney, Agent, or Firm* — Lerner David LLP

(57) ABSTRACT

Methods for obtaining a carboxylic acid product from a lactose-containing feedstock include contacting the lactose-containing feedstock and a first mixture of microorganisms in a first bioreactor under anaerobic conditions at a temperature of about 45° C. to about 55° C. and a pH of from about 4 to about 6 for a period of time such that lactic acid is formed; contacting the lactic acid with a second mixture of microorganisms in a second bioreactor under anaerobic conditions at a temperature of about 25° C. to about 35° C. and a pH of from about 4 to about 6 for a period of time such that the lactic acid is converted to one or more $C_3$-$C_{12}$ carboxylic acid products; and isolating the one or more $C_3$-$C_{12}$ carboxylic acid products. The lactose-containing feedstock has a pH greater than 4.5.

19 Claims, 4 Drawing Sheets

(56) References Cited

OTHER PUBLICATIONS

Anna Duber, et al.; "Lactate and Ethanol Chain Elongation in the Presence of Lactose: Insight into Product Selectivity and Microbiome Composition"; ACS Sustainable Chem. Eng. 2022, 10, 3407-3416; pp. 3407-3416; Mar. 7, 2022.

* cited by examiner

MICROBIAL CONVERSION OF LACTOSE-CONTAINING FEEDSTOCKS TO CARBOXYLIC ACIDS

CROSS REFERENCE TO RELATED APPLICATIONS

This application is a bypass continuation of PCT International Application No. PCT/US2020/019534, filed Feb. 24, 2020, which claims priority to U.S. Provisional Application No. 62/809,685, filed Feb. 24, 2019, the disclosure of each of which is incorporated herein in its entirety by express reference thereto.

FIELD OF THE DISCLOSURE

This disclosure relates to methods for obtaining a carboxylic acid product from a lactose-containing feedstock, particularly a non-acidic lactose-containing feedstock.

BACKGROUND OF THE DISCLOSURE

Many by-products are a nuisance to the dairy industry, limiting its growth because of environmental problems that these by-products cause, especially those related to getting rid of the whey and/or other by-products, such as the permeate resulting from the extraction of whey proteins.

Anaerobic fermentation can convert carbohydrates into lactic acid. Lactic acid, in turn, can be converted to longer chain carboxylic acids. Carboxylic acids, and in particular medium-chain carboxylic acids, such as n-caproic acid, are chemicals that can be used in the production of fragrances, pharmaceuticals, feed additives, antimicrobials, lubricants, rubbers, and dyes.

Thus, more efficient and economically feasible methods for producing carboxylic acids are needed.

SUMMARY OF THE DISCLOSURE

In a first aspect, the present disclosure encompasses a method for obtaining a carboxylic acid product from a lactose-containing feedstock including contacting the lactose-containing feedstock and a first mixture of microorganisms in a first bioreactor under anaerobic conditions at a temperature of about 45° C. to about 55° C. and a pH of from about 4 to about 6 for a period of time such that lactic acid is formed, wherein the lactose-containing feedstock has a pH greater than 4.5, contacting the lactic acid with a second mixture of microorganisms in a second bioreactor under anaerobic conditions at a temperature of about 25° C. to about 35° C. and a pH of from about 4 to about 6 for a period of time such that the lactic acid is converted to one or more $C_3$-$C_{12}$ carboxylic acid products, and isolating the one or more $C_3$-$C_{12}$ carboxylic acid products.

In a second aspect, the disclosure encompasses a method for obtaining a carboxylic acid product from a lactose-containing feedstock that includes contacting the lactose-containing feedstock and a first mixture of microorganisms in a first bioreactor under anaerobic conditions at a temperature of about 50° C. and a pH of about 5 for a period of time such that lactic acid is formed, wherein the lactose-containing feedstock has a pH greater than about 5, contacting the lactic acid with a second mixture of microorganisms in a second bioreactor under anaerobic conditions at a temperature of about 30° C. and a pH of about 5 for a period of time such that the lactic acid is converted to one or more C3-C12 carboxylic acid products, isolating the one or more C3-C12 carboxylic acid products, and maintaining the pH of about 5 in the first bioreactor and the second bioreactor.

In a third aspect, the disclosure encompasses a method for obtaining a carboxylic acid product from a non-acidic lactose-containing feedstock including contacting the non-acidic lactose-containing feedstock and a first mixture of microorganisms in a first bioreactor under anaerobic conditions at a temperature of about 50° C. and a pH of about 5 for a period of time such that lactic acid is formed, wherein the non-acidic lactose-containing feedstock has a pH of about 6, contacting the lactic acid with a second mixture of microorganisms in a second bioreactor under anaerobic conditions at a temperature of about 30° C. and a pH of from about 5 for a period of time such that the lactic acid is converted to one or more $C_3$-$C_{12}$ carboxylic acid products, and isolating the one or more $C_3$-$C_{12}$ carboxylic acid products.

Various embodiments are discussed below, which may be alternatively or additively combined with each other, along with any one of the three aspects described above. In one embodiment, the lactose-containing feedstock has a pH greater than about 5, and the pH of the lactose-containing feedstock is greater than the pH in the first bioreactor. In a preferred embodiment, the lactose-containing feedstock has a pH greater than about 6. In another preferred embodiment, the lactose-containing feedstock includes non-acidic lactose-containing feedstock. In a preferred embodiment, the non-acidic lactose-containing feedstock includes milk or cheese permeate. In various embodiments, the one or more $C_3$-$C_{12}$ carboxylic acid products include valeric acid, propionic acid, butyric acid, caproic acid, heptanoic acid, caprylic acid, nonanoic acid, decanoic acid or a combination thereof. In another embodiment, the method further includes retaining or adding a portion of the one or more $C_3$-$C_{12}$ carboxylic acid products in the second bioreactor. In yet another embodiment, isolating the one or more $C_3$-$C_{12}$ carboxylic acid products includes extracting the one or more $C_3$-$C_{12}$ carboxylic acid products by pertraction with a hydrophobic solvent and an alkaline extraction solution. In a preferred embodiment, the hydrophobic solvent includes mineral oil with trioctylphosphine oxide, and the alkaline extraction solution includes an aqueous solution of boric acid.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION OF THE DISCLOSURE

Figure 1A:
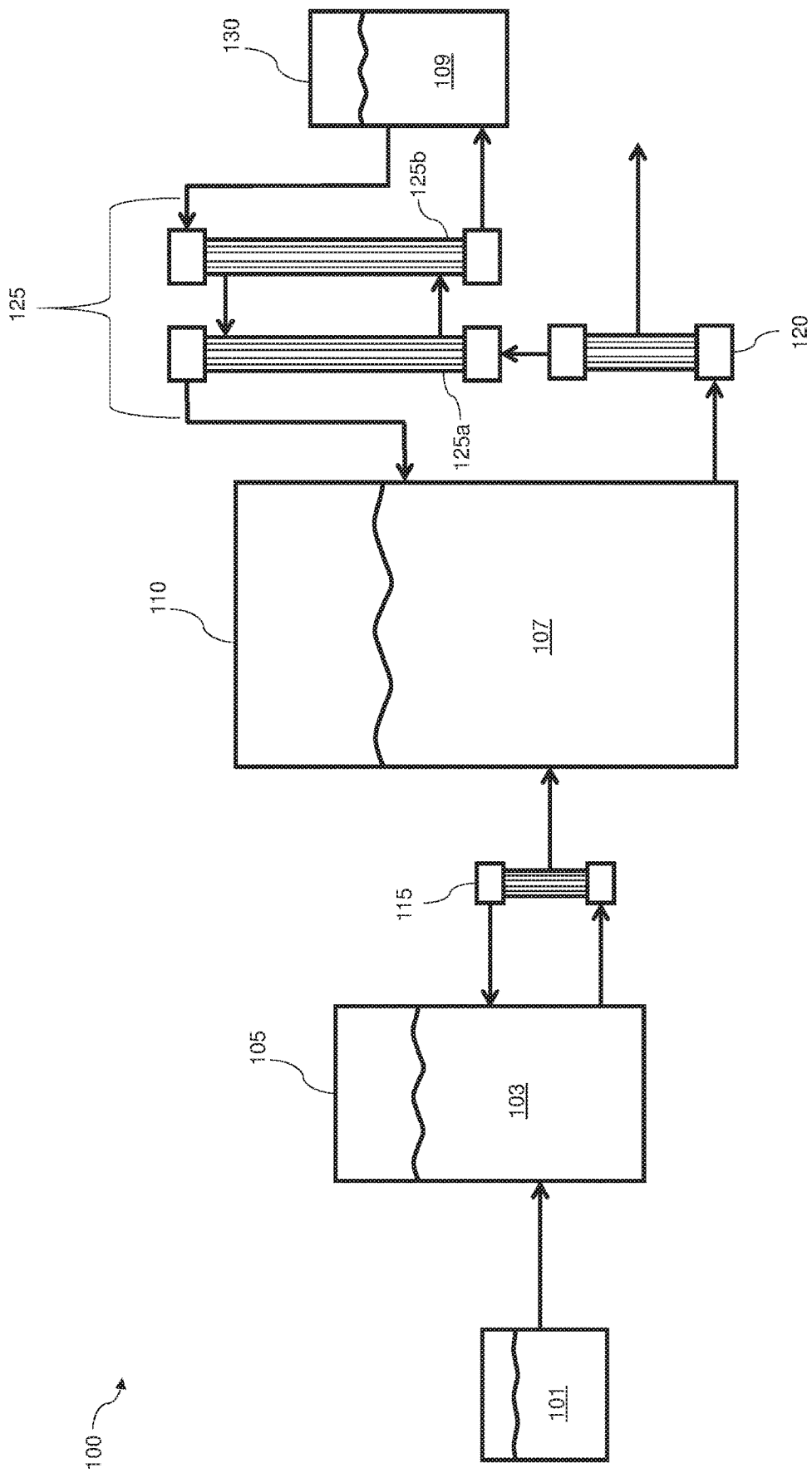
FIG. 1A is a schematic of a system capable of performing the methods according to an embodiment of the present invention.

The present invention provides methods and systems for producing and sequestering carboxylic acid products from a biological conversion process using microbial mixtures under a controlled environment. Carboxylic acids are weak organic acids with at least one carboxyl group, and the term "carboxylic acids" as used herein is meant include both the undissociated acid and the dissociated species of such acids. In addition, when a specific carboxylic acid is mentioned, it should be understood that its dissociated ion is also included. For example, as used herein, "lactic acid" is generally meant to encompass both lactic acid and its dissociated anion lactate.

The method includes mixing microorganisms with lactose-containing feedstock under conditions such that small and medium chain carboxylic acids (e.g., $C_3$ to $C_{12}$ carboxylic acids) are produced and isolated. In an exemplary embodiment, the method involves producing lactic acid from lactose-containing feedstock, and elongating the lactic acid to more hydrophobic, extractable medium-chain carboxylic acids. The methods take place without the addition of an external electron donor, such as alcohol.

Advantageously, exogenous alcohol is not required for the microorganisms to yield carboxylic acid products. Moreover, the methods described herein can successfully convert non-acidic lactose-containing feedstocks (e.g., dairy permeate, which is considerably different from whey) into carboxylic acid products. Accordingly, a wide variety of lactose-containing feedstocks (including feedstocks having a neutral or more basic pH) can be used in the present methods to provide carboxylic acid products.

The present methods may be conducted in one or more bioreactors under anaerobic conditions. For example, anaerobic conditions can be achieved by sealing the bioreactor and the system except to allow products (both liquid products and gas products) to be separated or escape. As used herein, "bioreactor" refers to a vessel, reactor, or any other container that supports a biologically active environment. The present methods may also be conducted in a continuous process or a batch process, or various portions of the process as a whole may be conducted with continuous or batch operation.

Lactose-containing feedstock is used as the starting material in the reactions. As used herein, "lactose-containing feedstock" means any type of feedstock including or containing lactose, lactic acid, or both. Sources of lactose-containing feedstock include, e.g., feedstock in liquid form such as acid whey, sweet whey, permeate, delactosed protein, milk, deproteinized whey, or modified whey, or solid feedstock such as milk dry solids, lactose powder, or dairy product solids. In some preferred embodiments, the lactose-containing feedstock is at least substantially free of, or entirely free of, lactose-based acid(s), added materials including acid, or a combination thereof. In some embodiments, the lactose-containing feedstock has a pH that is greater than about 4. In other embodiments, the lactose-containing feedstock has a pH that is greater than 4.5. In several embodiments, the lactose-containing feedstock has a pH greater than about 4 to about 4.5. In various embodiments, the lactose-containing feedstock has a pH greater than the operating pH of the first bioreactor. For example, in one embodiment, the lactose-containing feedstock has a pH greater than about 5, while the operating pH of the components in the bioreactor is lower. In certain embodiments, the lactose-containing feedstock has a pH of greater than about 5.5, while the operating pH in the bioreactor is below about 5.3. In various embodiments, the lactose-containing feedstock has a pH greater than about 6, while the operating pH in the bioreactor is below about 5.8. Lactose-containing feedstock having the appropriate pH includes, for example, cheese permeate, cheese whey (aka sweet whey), delactosed protein, milk, deproteinized whey, whey, and any dairy products that are in powder form (e.g., milk dry solids, lactose powder, or dairy product solids).

The reactions involved in the present methods include: (1) degradation of sugar (lactose) into acid (lactic acid) and (2) chain elongation of the acid (lactic acid) into longer chain carboxylic acids. Lactic acid fermentation in preferred embodiments herein is an anaerobic metabolic process by which lactose (made up of glucose and galactose subunits) is converted into lactic acid. Chain elongation of lactic acid into longer medium chain carboxylic acids can take place via the reverse β-oxidation pathway.

In exemplary embodiments, methods for obtaining a carboxylic acid product from a lactose-containing feedstock, preferably a non-acidic lactose-containing feedstock, include: (1) contacting the lactose-containing feedstock and a first mixture of microorganisms in a first bioreactor under anaerobic conditions at a temperature of about 45° C. to about 55° C. and a pH of from about 4 to about 6 for a period of time such that lactic acid is formed; (2) contacting the lactic acid with a second mixture of microorganisms in a second bioreactor under anaerobic conditions at a temperature of about 25° C. to about 35° C. and a pH of from about 4 to about 6 for a period of time such that the lactic acid is converted to one or more $C_3$-$C_{12}$ carboxylic acid products, and (3) isolating the one or more $C_3$-$C_{12}$ carboxylic acid products. The isolation step may or may not take place under anaerobic conditions. In a preferred embodiment, the carboxylic acid products are extracted in a liquid-liquid extraction process (i.e., pertraction). Any suitable isolation method may be used including, e.g., distillation, ion chromatography, crystallization, and electrochemical extraction.

The steps described in the various embodiments and examples disclosed herein are sufficient to produce the carboxylic acid products. Thus, in one embodiment, the present methods consist essentially of a combination of the steps of the present methods disclosed herein. In another embodiment, the present methods consist of those steps.

The microorganisms in the first bioreactor are selected to effectively degrade the lactose in the lactose-containing feedstock into lactic acid. Thermophilic conditions (>45° C.) are present in the first bioreactor to optimize lactic acid production. In exemplary embodiments, the microorganisms in the first bioreactor are dominated by lactobacilli (>90%), where distinct *Lactobacillus* operational taxonomic units (OTUs) (*Lactobacillus* spp.) and preferably also a few other OTUS of microorganisms maintained at greater than 1% of the population. Similarly in other food-related fermentations producing lactic acid, *Lactobacillus* spp. has been found to dominate, representing near 98% of the overall microbial community.

The microorganisms in the second bioreactor are selected to effect chain elongation of the lactic acid into short and medium chain carboxylic acids. Mesophilic conditions (20° C. to about 45° C.) are present in the second bioreactor to optimize chain elongation with the reactor microbiomes. The substrate for the second bioreactor is typically the lactic acid-rich effluent from the first bioreactor. In exemplary embodiments, the microbial community in the second bioreactor are considerably more diverse and different from the community in the first bioreactor, although it is possible that there is some overlap in species. In various embodiments, the microorganisms in the second bioreactor are dominated (>90%) by 26 OTUs, each representing over 1% of the community: unknown Porphyromonadaceae, *Dysgonomonas* spp., unknown Bacteroidales, *Bacteroides* spp., unknown Clostridiales, *Clostridium tyrobutyricum. Ruminococcus* spp., *Clostridium* spp., unknown Lactobacillales, *Lactobacillus zeae, Lactobacillus* spp., unknown Microbacteriaeae, *Acetobacter* spp., *Rhodocyclaceae* K82 spp., unknown Xanthomonadaceae, and *Arcobacter* spp. Bacteroidales was present in the largest abundance, with an average above 20% and Clostridiales was present with an average above 10%.

Advantageously, pure cultures of microorganisms are not needed to carry out the present methods, although pure cultures can be used, and additionally, the inoculum source need not be sterile. As used herein, "inoculum source" means an original source of the microorganisms. The inoculum source does not limit the types and number of microorganisms present in the bioreactor, as bioreactor conditions can determine the final composition of microorganisms.

The microorganisms used in the present methods can be obtained from a number of inoculum sources such as one or more of: activated sludge, anaerobic digesters, acidogenic processes, rumen microbes, soil microorganisms, marine microorganisms, intestinal microorganisms (from animals or insects), and feces (human or animal), and any combination of any of the foregoing. In the present methods, the relative population of the microorganisms can be manipulated by controlling the pH, temperature, and mixture of microorganisms in the environment. Adjustment of these parameters often causes certain parts of the microbial community to shift their metabolism to maintain optimum growth and productivity.

The products formed from the present methods include a liquid carboxylic acid component and a gaseous component. The liquid component can contain, for example, $C_3$-$C_{12}$ carboxylic acids, methane, or a combination thereof. The gaseous component of the product can include methane, hydrogen, carbon dioxide, or a combination thereof. In several embodiments, the gaseous components are produced in limited amounts (e.g., less than 1%).

In various embodiments, the carboxylic acid products are removed in a continuous manner from the system, as distinct from batch removal. In one embodiment, the carboxylic acid products are removed using in-line pertraction (membrane-based liquid-liquid extraction) with a hydrophobic solvent and an alkaline extraction solution. For example, the hydrophobic solvent can include mineral oil with a phosphine oxide (e.g., trioctylphosphine oxide (TOPO)). In an exemplary embodiment, the hydrophobic solvent includes mineral oil with about 2-4% TOPO, or specifically with about 3% TOPO. In various other embodiments, the hydrophobic solvent can include, for example, biodiesel, palm oil, tributylphosphine, trioctylamine, amines (primary, secondary, tertiary, etc.), aliquat solvents (e.g., tertiary and quaternary amines), phosphonium surfactants, ammonium surfactants, polyhydroxyalkanoates, hexane, vegetable oils, other organic solvents, and ionic liquids. In one embodiment, the alkaline extraction solution includes an aqueous solution of boric acid. In some embodiments, the alkaline extraction solution is maintained at a pH of about 8.5 to 9.5, such as pH of 9, with basic chemicals. Such basic chemicals include any routine buffering or pH-controlling chemicals.

The carboxylic acid products can be removed by methods other than membrane-based liquid pertraction methods. Any suitable method that can isolate the carboxylic acid products from the bioreactor mixture (e.g., broth) may be used. For example, harvesting of the carboxylic acid products may involve solvent extraction (with or without membranes) (e.g., non-membrane solvent extraction), distillation, electrochemical separation, crystallization, ion chromatography, or a combination thereof. Some extraction techniques may be more optimal when used in series with another (e.g., electrochemical separation with membrane solvent extraction).

Carboxylic acid removal or harvesting may be performed continuously, periodically, or at the end of a processing run, either on the recirculated broth of the bioreactors, or on the effluent as it leaves the system. In an exemplary embodiment, a continuous harvesting technique on reactor broth that is constantly circulating through the second bioreactor is used. This extraction can be energy intensive, so an alternative is to operate the extraction process periodically without a negative effect on the bioprocess. In periodic harvesting, the extraction can be turned on when energy costs are decreased (low-demand periods), allowing the bioprocess to be used for grid load-balancing at large scales. Further, carboxylic acid can be extracted from the effluent of a continuously-flowing bioprocess or from the final broth of a batch-operated bioprocess. The carboxylic acid harvesting technique can involve the above-described methods (singly and/or concurrently), and other suitable methods.

In several embodiments, the present methods can be carried out indefinitely (e.g., years) with hydraulic retention times of from about 0.25 days to about 40 days. The hydraulic retention time is the time the microorganisms contact the substrate (e.g., lactose-containing feedstock and lactic acid) to effect a desired production of the carboxylic acid products. In one embodiment, the hydraulic retention time can be from about 0.25 days to about 15 days. It may be necessary to periodically replenish one or more species of microorganism in one or both bioreactors to ensure a sufficient quantity to conduct efficient operations.

The carboxylic acids produced by the present methods can be used for various conventional applications. Additionally, the carboxylic acids can be converted into alkanes for biofuels. For example, the carboxylic acids can be converted to alkanes by a subsequent abiotic process (e.g., ketonization).

Figure 1B:
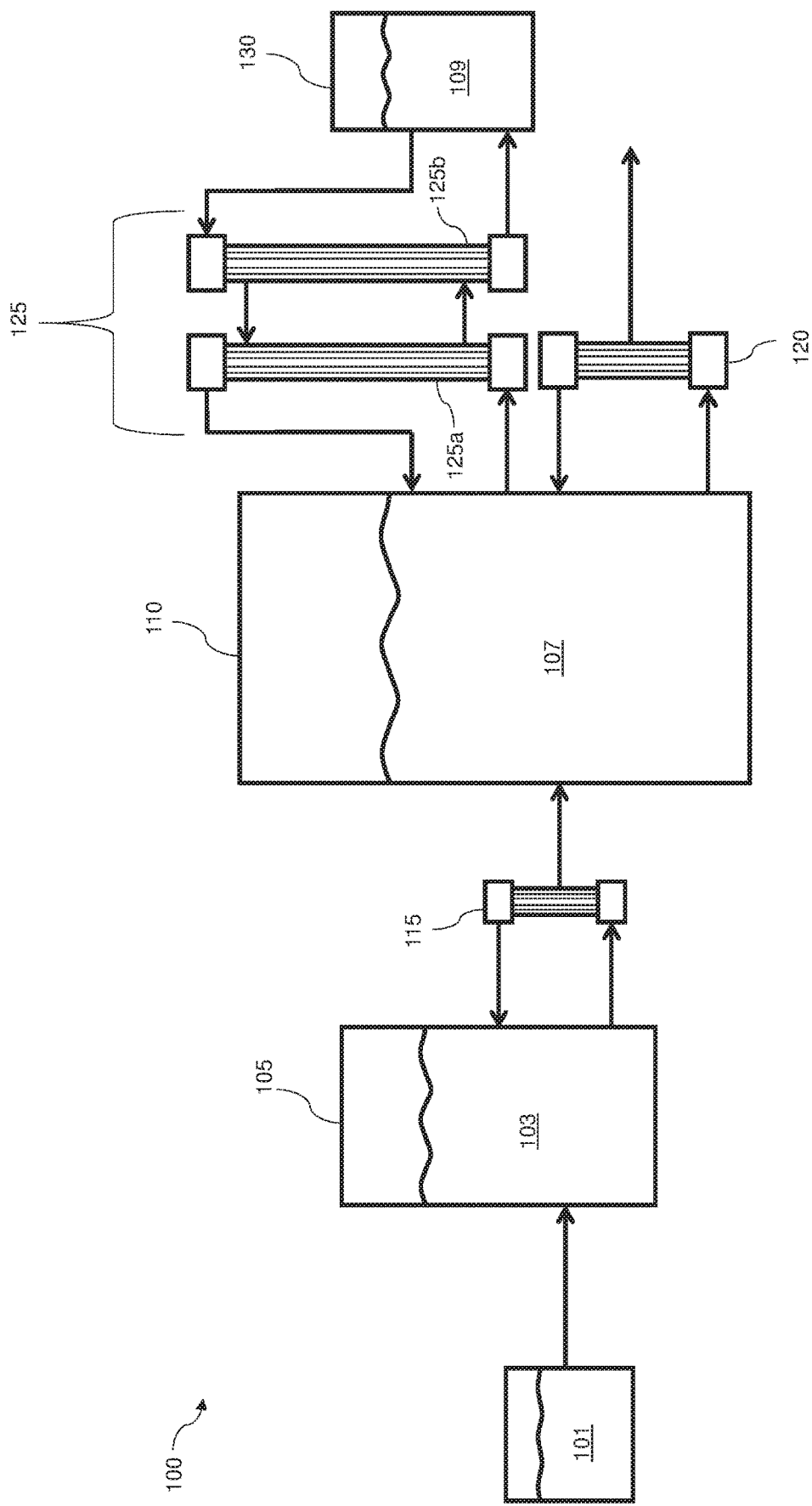
FIG. 1B is a schematic of another system capable of performing the methods according to an embodiment of the present invention.

Referring now to FIGS. 1A and 1B, shown are exemplary systems 100 for performing the present methods. FIG. 1A shows a system 100 where product extraction device 125 and microbial biomass retention device 120 are in series, while FIG. 1B shows a system 100 where product extraction device 125 and microbial biomass retention device 120 are in parallel.

As shown systems 100 include two bioreactors 105, 110. Although not shown, it should be understood that additional bioreactors (e.g., a third bioreactor placed in series after second bioreactor 110) for converting lactic acid to longer chain carboxylic acid may be included in systems 100 to increase the extent of conversion and minimize post-treatment of the effluent.

The first phase of the present methods is conducted in a bioreactor, preferably under anaerobic conditions. Therefore, in certain embodiments, bioreactors 105, 110 are sealed except to allow products (both liquid and gas products) to be separated or escape. The bioreactors 105, 110 can be made of a number of different materials. For example, the bioreactors 105, 110 can be glass or stainless steel and constructed as to prevent diffusion through fittings and withstand pressurization. Bioreactors 105, 110 can have their contents mixed periodically to promote substrate-microorganism contact, thereby increasing the yield and rate of various conversions and reactions according to the present disclosure. To this end, either or both of the bioreactors 105, 110 may be constructed including relevant mixing equipment, or with batch operation a bioreactor can be halted, the contents mixed with external mixing equipment, e.g., in a nitrogen environment, then and if needed have the oxygen blown off and the processing continued.

In several embodiments, bioreactors 105, 110 each include a pH controller configured to independently maintain a pH of the contents of first and second bioreactors 105, 110 to about 5. The pH controller can include a pH probe that can be positioned to monitor the pH of the respective broths 103, 107. The pH controller can be one in which the pH can be controlled by measuring the pH and adjusting the pH accordingly through addition of an acid or a base.

In certain embodiments, bioreactors 105, 110 each include a temperature controller. The temperature controller of bioreactor 105 may be configured to maintain the temperature of bioreactor 105 to about 50° C., or as otherwise stated herein. The temperature controller of bioreactor 110 may be configured to maintain the temperature of bioreactor 110 to about 30° C., or as otherwise stated herein. In some embodiments, the temperature controller includes a heating/cooling jacket covering at least a portion of bioreactors 105, 110, a heating/cooling element within bioreactors 105, 110, a heating/cooling heat exchanger in the recirculation line of bioreactors 105, 110, or a heating/cooling element underneath bioreactors 105, 110, or any combination thereof to provide for desired heating, cooling, or both, for each bioreactor.

In various embodiments, internal packing architectures are included in bioreactors 105, 110 to add surface area to help retain microorganism biomass. For example, ceramic or plastic packing materials may be placed within one or both bioreactors 105, 110.

Systems 100 also include one or more microbial biomass retention devices 115, 120 to control microorganism cell loss particularly when operation is under continuous flow. In an exemplary embodiment, the biomass retention devices 115, 120 can include tangential flow filter (TFF) membranes to prevent biomass from escaping the bioprocess. The TFF membranes may be formed from any suitable material including glass fiber, polycarbonate, cellulose, nitrocellulose, nylon, rayon, polyester, e.g., Dacron®, or the like, or a combination of any of the foregoing. The TFF membranes help to start up the bioprocess, maintain slow-growing microorganisms that have not attached to the packing architecture, and/or rebuild the biomass after accidental changes to systems 100. In an exemplary embodiment, the pore size of the TFF membrane is less than about 0.22 µm, though the pore size may be any suitable size that can retain all or substantially all of the relevant microorganisms.

Systems 100 further include a product extraction device 125 configured to isolate the formed carboxylic acids. Product extraction device 125 of the systems 100 can be a membrane-based pertraction device, a non-membrane solvent extraction device, a distillation device, an electrochemical device, an ion chromatography device, or any combination thereof, such as arranged in series. In one embodiment, product extraction device 125 operates continuously.

In the exemplary embodiments shown in FIGS. 1A and 1B, product extraction device 125 includes a membrane-based pertraction device. As shown, the pertraction device includes two membranes to extract the carboxylic acid products. The first membrane 125a contacts effluent from bioreactor 110 with a hydrophobic solvent (e.g., mineral oil and 3% TOPO solvent). The hydrophobic solvent is then transferred across the second membrane 125b to an alkaline extraction solution 109. Alkaline extraction solution 109 may be an aqueous solution of boric acid. The solution 109 can be maintained at a pH of about 8.5 to about 9.5, with an exemplary pH at about 9. Carboxylic acids accumulate in alkaline extraction solution 109.

Finally, systems 100 each include a concentration vessel 130 holding alkaline extraction solution 109, which is configured to store the carboxylic acids that are produced. Over time, alkaline extraction solution 109 becomes concentrated with carboxylic acids, at which point the pH can be lowered to a pH of about 4.5 to drive phase separation. This forms a high purity (>90%) end product that floats to the top of the solution 109 to facilitate separation and removal. This phase separation process can be performed periodically in batch or in a continuous fashion with an additional unit.

The present methods will now be described with respect to systems 100 in FIGS. 1A and 1B. Lactose-containing feedstock 101 (either in liquid or solid form) is fed into a well-mixed bioreactor 105 containing a targeted community of microorganisms. Bioreactor 105 is operated at about 50° C. and a pH of about 5. The flowrate of the feedstock 101 is optimized to maximize the microbial conversion of lactose to lactic acid. In some embodiments, the flowrate is about 100 gallons of feedstock/100 gallons of the bioreactor up to about 200 gallons of feedstock/100 gallons of the bioreactor. The hydraulic residence time in the bioreactor 105 ranges from about 0.25 days to about 5 days to effect conversion of lactose to lactic acid.

The lactose-containing feedstock 101 generally has a pH that is higher than the operating pH of 5 in bioreactor 105. The pH of the broth 103 may be adjusted by base chemicals, such as sodium hydroxide (NaOH), or acid chemicals, such as hydrochloric acid (HCl) and/or sulfuric acid ($H_2SO_4$). In one embodiment, the pH of the broth 103 does not need to be adjusted because of the pH of the lactose-containing feedstock 101. In embodiments where the lactose-containing feedstock 101 is provided in liquid form, bioreactor 105 may contain only the community of microorganisms (without additional water).

Cells are separated from the effluent stream exiting bioreactor 105 using biomass retention device 115 to minimize or prevent biomass from escaping the process. The cells are returned to bioreactor 105 or discarded to maintain target biomass levels. The biomass retention device 115 may be designed to permit certain microbes to pass to bioreactor 110, as well. Any produced gas in bioreactor 105 is flowed out of bioreactor 105 through an air-lock (or one-way valve or other similar equipment). Produced gas includes carbon dioxide, hydrogen, and methane, in minimal amounts. The cell-free lactic acid-rich effluent is then fed to bioreactor 110.

Bioreactor 110 is a well-mixed bioreactor operated at about 30° C. and pH of about 5. Acid chemicals (e.g., HCl, $H_2SO_4$, or carboxylic acid product) are added to maintain the pH of broth 107. The flowrate of effluent into bioreactor 110 is about 25 gallons of effluent/100 gallons of reactor, and is optimized to maximize the microbial conversion of lactic acid to carboxylic acid product. Hydraulic residence time in bioreactor 110 ranges from about 0.5 days to about 16 days.

Cells are separated from the effluent stream exiting bioreactor 110 using biomass retention device 120, and the cells are returned to bioreactor 110 or discarded to maintain target biomass levels. Any produced gas is flowed out of the bioreactor 110 through an air lock (or one-way valve or other similar equipment). The pH in bioreactor 110 can be controlled by returning carboxylic acid product back into bioreactor 110. FIG. 1A shows a single recirculation loop flowing broth through biomass retention device 120 into product extraction device 125, flowing in series. FIG. 1B shows two recirculation loops operating through biomass retention device 120 and product extraction device 125, which are independent of each other. In both FIGS. 1A and 1B, the cell-free effluent is discarded. In various embodiments, a second or further product extraction device can be added to extract more carboxylic acids.

As shown, product extraction device 125 includes two membranes 125a, 125b to extract the carboxylic acids by pertraction. Effluent enters the first membrane 125a and is contacted with a hydrophobic solvent (e.g., mineral oil with TOPO). Carboxylic acids are extracted into the hydrophobic solvent because of their increased solubility in the solvent. The solvent containing the carboxylic acids then enters the second membrane 125b and is contacted with alkaline extraction solution 109 (e.g., aqueous boric acid solution at a pH of about 9) provided by concentration vessel 130. Carboxylic acids are extracted into alkaline extraction solution 109 and moved into concentration vessel 130. Aliquots of the alkaline extraction solution 109 will be periodically removed to have pH lowered to drive phase separation and facilitate removal of the desired carboxylic acid(s). Upon removal of desired carboxylic acids, the alkaline extraction solution 109 can be returned to the concentration vessel 130 or discarded.

Approaches to retain cells with biomass retention devices 115, 120 may be altered in the future to address larger scales by transitioning from the TFF architecture towards single-pass-through filters. In this embodiment, cells retained by the filter may be discarded, repurposed, or returned back to bioreactor 105, 110 periodically.

The bioreactor 105, 110 architecture may be altered to address engineering requirements at larger scales by adopting high-rate fermentation practices for anaerobic wastewater treatment, such as continuously stirred-tank, anaerobic biofilm, upflow anaerobic sludge blanket, anaerobic sequencing batch bioreactors.

Based on the typical flowrates listed above for bioreactor 105, 110, arrangements to maximize performance may lead to systems with bioreactors in series and parallel. In particular, no difficulty is expected to parallelize the operation of bioreactors 105, 110. Bioreactor 110, however, shows promise for performance improvements by operating multiple bioreactors in series; with this arrangement, the need to install a product extraction device 125 on each of the bioreactors may not be necessary.

Post-treatment of the cell-free effluent is expected to be necessary for proper disposal. One approach to lower the treatment level and increase carboxylic acid production is to feed the effluent to an additional product extraction device to remove all product from the effluent and lower the effluent organic concentration.

In one embodiment, the feedstock is essentially or entirely free of ethanol, preferably essentially or entirely free of ethanol and methanol, and more preferably essentially or entirely free of alcohol. In another embodiment, one or both bioreactors are essentially or entirely free of ethanol, and more preferably essentially or entirely free of alcohol. Both embodiments may be combined in yet another aspect of the disclosure.

The following examples are illustrative of the systems and methods discussed above and are not intended to be limiting.

Example 1

Milk Permeate

Figure 2:
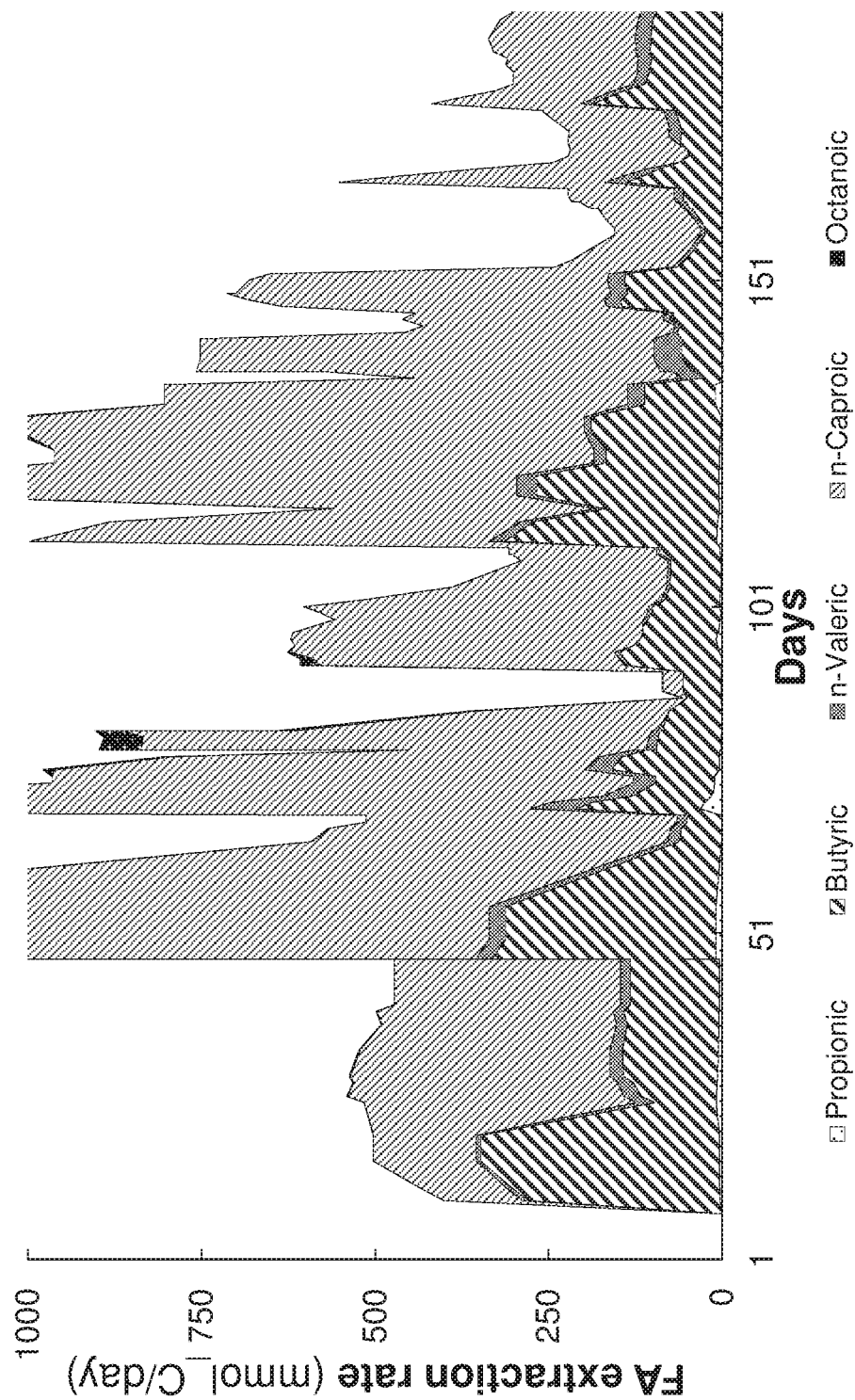
FIG. 2 illustrates the production rate from a bioprocess fed with milk permeate according to an embodiment of the present invention.

The data illustrated in FIG. 2 was collected by continuously feeding milk permeate into a method and system as described above. The system was recirculated at about 100 mL/minute.

Various flowrates, dilution concentrations, and system parameters were evaluated to optimize production rates, treatment rates, and treatment extent. The first and second bioreactors were custom made from PVC pipe. The first bioreactor had a 1000 mL liquid volume capacity with ceramic/porcelain beads at the bottom. The second bioreactor had a 4000 mL liquid volume capacity with ceramic/porcelain beads at the bottom.

Nominally, 250 mL/day of undiluted milk permeate was fed into the first bioreactor. The first bioreactor was kept at 50° C. and a pH of 5. The hydraulic retention time of the milk permeate in the first bioreactor was 4 days. The second bioreactor was kept at 30° C. and a pH of 5. The hydraulic retention time of the lactic acid-rich effluent in the second bioreactor was 16 days. A continuous liquid pertraction method was used to isolate the carboxylic acid products. The hydrophobic solvent used was mineral oil with about 3% TOPO, and the alkaline extraction solution was an aqueous solution of boric acid maintained at a pH of 9.

The data in FIG. 2 was generated from analyzing samples from the alkaline extraction solution over time via gas chromatography. The data shown represents the 5 carboxylic acids having the highest concentrations that were observed.

Example 2

Acid Whey

Figure 3:
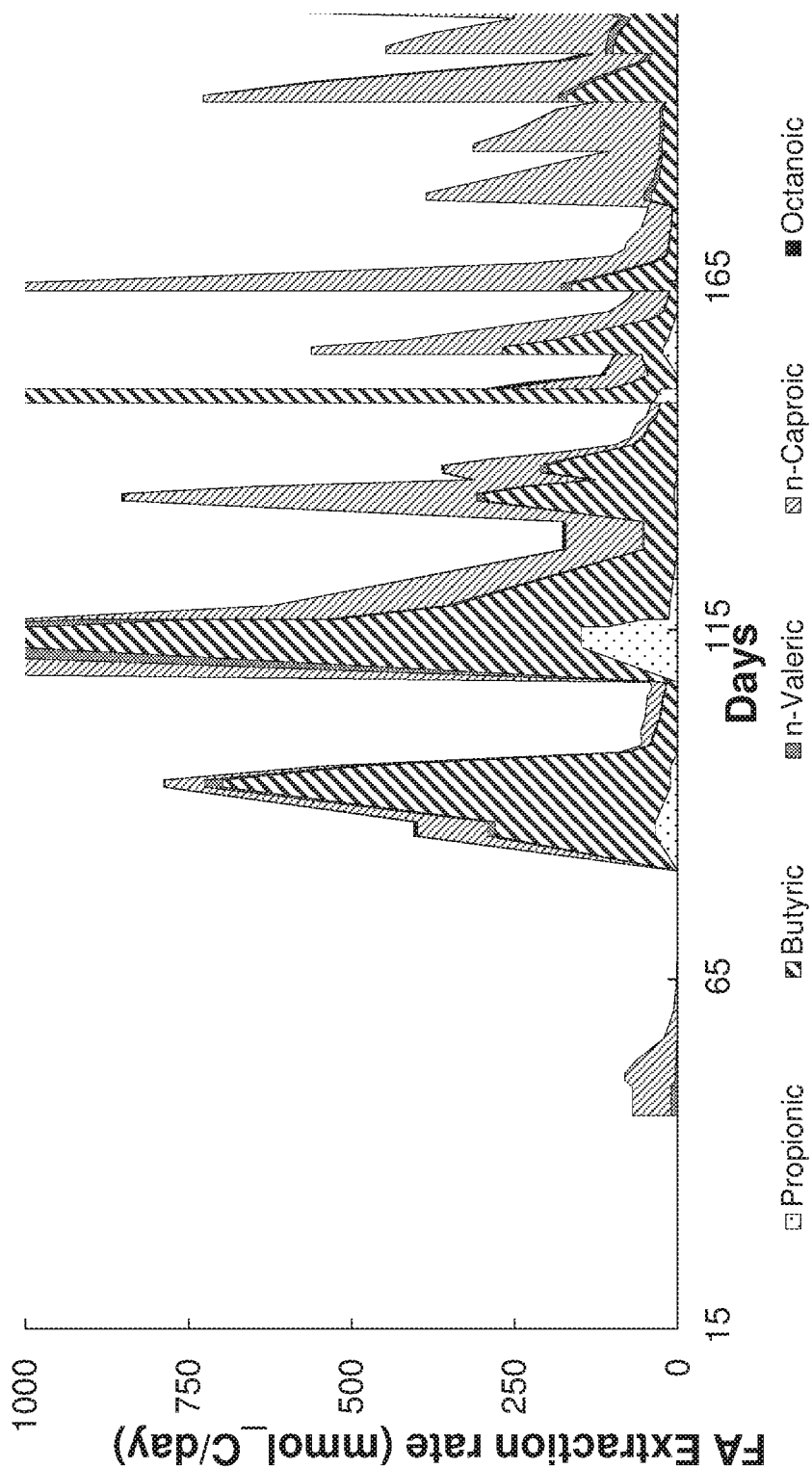
FIG. 3 illustrates the production rate from a bioprocess fed with acid whey.

The data illustrated in FIG. 3 was collected by continuously feeding acid whey into a method and system as described above. The system was recirculated at about 100 mL/minute.

Various flowrates, dilution concentrations, and system parameters were evaluated to optimize production rates, treatment rates, and treatment extents. The first and second bioreactors were custom made from PVC pipe. The first bioreactor had a 1000 mL liquid volume capacity with ceramic/porcelain beads at the bottom. The second bioreactor had a 4000 mL liquid volume capacity with ceramic/porcelain beads at the bottom.

Nominally, 1000 mL/day of undiluted acid whey was fed into the first bioreactor. The first bioreactor was kept at 50° C. and a pH of 5. The hydraulic retention time of the acid whey in the first bioreactor was 1 day. The second bioreactor was kept at 30° C. and a pH of 5. The hydraulic retention time of the lactic acid-rich effluent in the second bioreactor was 4 days. A continuous liquid pertraction method was used to isolate the carboxylic acid products. The hydrophobic solvent used was mineral oil with about 3% TOPO, and the alkaline extraction solution was an aqueous solution of boric acid maintained at a pH of 9.

The data in FIG. 3 was generated from analyzing samples from the alkaline extraction solution over time via gas chromatography. The data shown represents the 5 carboxylic acids having the highest concentrations that were observed.

As can be seen from a comparison of FIGS. 2 and 3, higher production rates of carboxylic acid were obtained from the milk permeate than from the acid whey.

Although only a few exemplary embodiments have been described in detail above, those of ordinary skill in the art will readily appreciate that many other modifications are possible in the exemplary embodiments without materially departing from the novel teachings and advantages of the present invention. Accordingly, all such modifications are intended to be included within the scope of the present invention as defined in the following claims.

What is claimed is:

1. A method for obtaining a carboxylic acid product from a lactose-containing feedstock comprising:

contacting the lactose-containing feedstock having no acid whey and a first mixture of microorganisms comprising lactobacilli in a first bioreactor under anaerobic conditions at a temperature of 45° C. to 55° C. and a pH of from 4 to 6 for a period of time such that lactic acid is formed, wherein the lactose-containing feedstock consists of a feedstock having a pH greater than 4.5 and the lactose-containing feedstock is selected from the group consisting of dairy permeate, delactosed protein, milk, deproteinized whey, milk dry solids, lactose powder, dairy product solids, and mixtures thereof;

contacting the lactic acid with a second mixture of microorganisms comprising bacteria from the family Porphyromonadaceae, *Dysgonomonas* spp., bacteria from the order Bacteroidales, *Bacteroides* spp., bacteria from the order Clostridiales, *Clostridium tyrobutyricum*, *Ruminococcus* spp., *Clostridium* spp., bacteria from the order Lactobacillies, *Lactobacillus zeae*, *Lactobacillus* spp., bacteria from the family Microbacteriaeae, *Acetobacter* spp., *Rhodocyclaceae* K82 spp., bacteria from the family Xanthomonadaceae, and *Arcobacter* spp. in a second bioreactor under anaerobic conditions at a temperature of 20° C. to 45° C. and a pH of from 4 to 6 for a period of time such that the lactic acid is converted to one or more $C_3$-$C_{12}$ carboxylic acid products; and isolating the one or more $C_3$-$C_{12}$ carboxylic acid products.

2. The method of claim 1, wherein the lactose-containing feedstock has a pH greater than 5, and the pH of the lactose-containing feedstock is greater than the pH in the first bioreactor.

3. The method of claim 1, wherein the lactose-containing feedstock has a pH greater than 6.

4. The method of claim 1, wherein the one or more $C_3$-$C_{12}$ carboxylic acid products comprise valeric acid, propionic acid, butyric acid, caproic acid, heptanoic acid, caprylic acid, nonanoic acid, decanoic acid or a combination thereof.

5. The method of claim 1, further comprising retaining or adding a portion of the one or more $C_3$-$C_{12}$ carboxylic acid products in the second bioreactor.

6. The method of claim 1, wherein isolating the one or more $C_3$-$C_{12}$ carboxylic acid products comprises extracting the one or more $C_3$-$C_{12}$ carboxylic acid products by pertraction with a hydrophobic solvent and an alkaline extraction solution.

7. The method of claim 6, wherein the hydrophobic solvent comprises mineral oil with trioctylphosphine oxide, and the alkaline extraction solution comprises an aqueous solution of boric acid.

8. The method of claim 1, wherein the lactose-containing feedstock comprises dairy permeate, and the permeate comprises cheese permeate or milk permeate.

9. The method of claim 8, wherein the permeate comprises milk permeate.

10. A method for obtaining a carboxylic acid product from a lactose-containing feedstock comprising:

contacting the lactose-containing feedstock having no acid whey and a first mixture of microorganisms comprising lactobacilli in a first bioreactor under anaerobic conditions at a temperature of 50° C. and a pH of 5 for a period of time such that lactic acid is formed, wherein the lactose-containing feedstock consists of a feedstock having a pH greater than 5 and the lactose-containing feedstock comprises at least one of milk or cheese permeate;

contacting the lactic acid with a second mixture of microorganisms comprising bacteria from the family Porphyromonadaceae, *Dysgonomonas* spp., bacteria from the order Bacteroidales, *Bacteroides* spp., bacteria from the order Clostridiales, *Clostridium tyrobutyricum*, *Ruminococcus* spp., *Clostridium* spp., bacteria from the order Lactobacillies, *Lactobacillus zeae*, *Lactobacillus* spp., bacteria from the family Microbacteriaeae, *Acetobacter* spp., *Rhodocyclaceae* K82 spp., bacteria from the family Xanthomonadaceae, and *Arcobacter* spp. in a second bioreactor under anaerobic conditions at a temperature of 30° C. and a pH of 5 for a period of time such that the lactic acid is converted to one or more $C_3$-$C_{12}$ carboxylic acid products;

isolating the one or more $C_3$-$C_{12}$ carboxylic acid products;

maintaining the pH of 5 in the first bioreactor and the second bioreactor; and wherein higher production rates of carboxylic acid are obtained from the lactose containing feedstock as compared to acid whey feedstock.

11. The method of claim 10, wherein the lactose-containing feedstock has a pH greater than 6, and the pH of the lactose-containing feedstock is greater than the pH in the first bioreactor.

12. The method of claim 10, wherein the one or more $C_3$-$C_{12}$ carboxylic acid products comprise caproic acid, caprylic acid, nonanoic acid, or a combination thereof.

13. The method of claim 10, further comprising adding a portion of the one or more $C_3$-$C_{12}$ carboxylic acid products into the second bioreactor to maintain the pH of 5.

14. The method of claim 10, wherein isolating the one or more $C_3$-$C_{12}$ carboxylic acid products comprises extracting the one or more $C_3$-$C_{12}$ carboxylic acid products by pertraction with a hydrophobic solvent and an alkaline extraction solution.

15. The method of claim 14, wherein the hydrophobic solvent comprises mineral oil with trioctylphosphine oxide, and the alkaline extraction solution comprises an aqueous solution of boric acid.

16. The method of claim 10, wherein the lactose-containing feedstock comprises milk permeate.

17. A method for obtaining a carboxylic acid product from a lactose-containing feedstock comprising:

contacting the lactose-containing feedstock having no acid whey and a first mixture of microorganisms comprising lactobacilli in a first bioreactor under anaerobic conditions at a temperature of 50° C. and a pH of 5 for a period of time such that lactic acid is formed, wherein the lactose-containing feedstock consists of a feedstock having a pH greater than 6 and the lactose-containing feedstock comprises at least one of milk or cheese permeate;

contacting the lactic acid with a second mixture of microorganisms comprising bacteria from the family Porphyromonadaceae, *Dysgonomonas* spp., bacteria from the order Bacteroidales, *Bacteroides* spp., bacteria from the order Clostridiales, *Clostridium tyrobutyricum*, *Ruminococcus* spp., *Clostridium* spp., bacteria from the order Lactobacillies, *Lactobacillus zeae*, *Lactobacillus* spp., bacteria from the family Microbacteriaeae, *Acetobacter* spp., *Rhodocyclaceae* K82 spp., bacteria from the family Xanthomonadaceae, and *Arcobacter* spp. in a second bioreactor under anaerobic conditions at a temperature of 30° C. and a pH of 5 for a period of time such that the lactic acid is converted to one or more $C_3$-$C_{12}$ carboxylic acid products;

isolating the one or more $C_3$-$C_{12}$ carboxylic acid products; and wherein higher production rates of carboxylic acid are obtained from the lactose containing feedstock as compared to acid whey feedstock.

18. The method of claim 17, further comprising retaining or adding a portion of the one or more $C_3$-$C_{12}$ carboxylic acid products into the second bioreactor.

19. The method of claim 17, wherein the lactose-containing feedstock comprises milk permeate.

\* \* \* \* \*